US006694268B2

(12) United States Patent
Maruyama

(10) Patent No.: US 6,694,268 B2
(45) Date of Patent: Feb. 17, 2004

(54) LEAKAGE INSPECTION METHOD FOR SEALED CONTAINER AND APPARATUS FOR CARRYING OUT THE METHOD

(75) Inventor: Tomoyuki Maruyama, Tokyo (JP)

(73) Assignee: Rieckermann (Japan) Ltd., Tokyo (JP)

( * ) Notice: Subject to any disclaimer, the term of this patent is extended or adjusted under 35 U.S.C. 154(b) by 43 days.

(21) Appl. No.: 10/167,129

(22) Filed: Jun. 11, 2002

(65) Prior Publication Data

US 2002/0193951 A1 Dec. 19, 2002

(30) Foreign Application Priority Data

Jun. 15, 2001 (JP) ........................................ 2001-181487

(51) Int. Cl.$^7$ .......................... G01N 27/20; G01N 27/02
(52) U.S. Cl. ............................. 702/51; 73/799; 73/49.3; 324/557
(58) Field of Search .............................. 702/51; 73/763, 73/799, 40, 49.3; 324/557, 559; 340/71.1, 605

(56) References Cited

U.S. PATENT DOCUMENTS

| 4,914,395 | A |   | 4/1990  | Hamada       | 324/557 |
|-----------|---|---|---------|--------------|---------|
| 5,760,295 | A | * | 6/1998  | Yasumoto     | 73/49.3 |
| 5,850,144 | A | * | 12/1998 | Howells et al. | 324/559 |
| 6,593,752 | B1| * | 7/2003  | Yasumoto     | 324/557 |

FOREIGN PATENT DOCUMENTS

| JP | 58-182548 | 10/1983 |
| JP | 63-101728 | 5/1988 |
| JP | 63-150641 | 6/1988 |
| JP | 01-272954 | 10/1989 |
| JP | 01-287454 | 11/1989 |

* cited by examiner

*Primary Examiner*—Kamini Shah
(74) *Attorney, Agent, or Firm*—Pearne & Gordon LLP

(57) ABSTRACT

A leakage inspection method for a sealed container in which a liquid of a non-electrolyte is contained for judging whether a defect exists in the container, the method comprising the steps of applying an inspection AC voltage through electrodes from an inspection power source unit; detecting an AC current flowing through the container and the contained liquid by means of a current detector; obtaining a digital value corresponding to an absolute value of the instantaneous value of the detected AC current; successively totaling the digital values during a totaling period having a specific relation to the waveform of the AC current whereby the total value of the digital values corresponding to the absolute values of the respective instantaneous values of the AC current is arithmetically operated and judging that the defect exists in the container when the total value as the value to be judged is larger than a setting value.

10 Claims, 7 Drawing Sheets

LEAKAGE INSPECTION METHOD FOR SEALED CONTAINER AND APPARATUS FOR CARRYING OUT THE METHOD

TECHNICAL FIELD OF THE INVENTION

This invention pertains to a leakage inspection method for a sealed container in which a liquid is liquid-tightly contained for inspecting whether a defect such as a pinhole or a crack causing a leakage of the liquid exists in the container and a leakage inspection apparatus for carrying out the leakage inspection method.

BACKGROUND OF THE INVENTION

A liquid such as an injection and an eye lotion that is required to avoid contamination by bacteria and deterioration by oxidization etc. is liquid-tightly preserved in a container formed of glass or plastic materials. The container to contain this kind of liquid is not allowed to have leakage. To this end, in the manufacturing process of products such as a medicine which should be shipped in a sealing manner, it is required to inspect whether a leakage generating a defect such as a pinhole or a crack, etc exists in the container or not.

In order to inspect the leakage of the sealed container formed of an insulating material such as a glass, a plastic material or the like in which the liquid is contained, there is known a method of observing a discharge phenomenon generated when an inspection voltage of AC high voltage is applied across the container.

As electrodes are put onto two places (inspection parts) of an outer surface of the insulating container in which the electrolytic liquid is contained and the AC high voltage is applied across the electrodes as the inspection voltage, an AC current flows through an electrostatic capacitance between the electrodes and the liquid in the container and through the liquid in the container. In this case, as a crest value of the inspection voltage is set up at a proper value, if the defect which causes the leakage in the inspection part does not exist, a feeble current just flows, but if the defect such as the pinhole or the crack exist in the inspection part and the leakage arises, or if the leakage may possibly arise, an electric discharge arises in the defective portion, and the current which flows across the electrodes increases. Thus, in the case where the liquid in the container is an electrolyte, whether the defect that causes the leakage exists in the inspection part where the electrodes are put from the crest value of the current flowing through the electrodes can be detected.

In the prior art inspection method, the AC current flowing through the electrodes placed onto the container to be inspected and through the container and the contained liquid is detected by a current detection resistance inserted in series to the grounded electrode and the crest value of the thus detected AC current is compared with a threshold value to judge that the leakage causing the defect exists when the crest value of the AC current is higher than the threshold value.

In the case where the liquid in the container is a non-electrolyte having a high resistance, even though the AC high voltage as the inspection voltage is applied across the container, the electric discharge never occurs across the defective portion and a fore-discharge phenomenon is just generated. In this state, since the comparative value relation between the crest value of the current detected when the defect exists and the crest value of the current detected when the defect does not exist is unfixed and in addition thereto, since the difference between the crest value of the current detected when the defect does not exist and the crest value of the current detected when the defect exists cannot be made large, the prior art method in which the crest value of the AC current flowing when the inspection voltage is applied is compared with the threshold value cannot clearly judge the existence of the defect.

In the case where the liquid in the container is the electrolyte having the lower resistance, the existence of the defect can be detected by comparing the crest value of the detected AC current with the threshold value. However, in the case where the liquid in the container is the electrolyte, even though there is no defect in the container, the momentary discharge is generated due to conditions such as a circumference environment, an existence of containment of the surface of the container, etc. so that the pulse noise overlaps the detected current waveform, which possibly causes the misjudgment of the existence of the defect or the mistaking of a good container for an inferior container. Although it is considered that the threshold value for the judgment is made higher in order to avoid such a misjudgment, the ratio of the inferior articles relative to the good articles will undesirably get higher by using the higher threshold value.

On the other hand, if the threshold value for the judgment of the quality is set up at a lower value so that the inspection is performed for a safety, the rate in which the good articles are judged as the inferior articles gets higher, the yield of the product is reduced and the high cost is caused.

Furthermore, in the case where the high voltage is applied across the insulating container formed of a glass, a plastic material etc., the quality of the container is possibly deteriorated and therefore the inspection voltage is desirably set up at a value as low as possible.

SUMMARY OF THE INVENTION

Accordingly, it is a principal object of the invention to provide a leakage inspection method for a sealed container adapted to detect an existence of a defect such as a pinhole or a crack with a high accuracy even though a liquid is either of an electrolyte or a non-electrolyte and to provide a leakage inspection apparatus used for carrying out such a leakage inspection method.

It is another object of the invention to provide a leakage inspection method for a sealed container adapted to perform an inspection even though a voltage used for the inspection is set up at a lower value with a high accuracy and to provide a leakage inspection apparatus used for carrying out such a leakage inspection method.

The present invention relates to a leakage inspection method having as an object of an inspection an insulating container in which a liquid is sealed and comprising the steps of applying an inspection voltage of high AC voltage across the container; detecting an AC current flowing through the container and the contained liquid and judging from a detection signal of the AC current whether there exists a defect in the container causing a leakage of the liquid.

In the invention, there is provided an A/D converter for converting an instantaneous value of the detection signal of the AC current into a digital value and there is arithmetically operated a total value of the digital values corresponding to the absolute values of the instantaneous values of the AC current detected during a specific totaling period having a specific relation to the waveform of the AC current. The total value as the value to be judged (referred to as "judgment value" later) is compared with a setting value and it is judged that the defect exists in the container when the total value exceeds the setting value.

The aforementioned totaling period is required to be the specific period always having the specific relation to the waveform of the AC current. There may be selected a period which can be detected on a easily detectable zero cross or peak point, such as period of positive half cycle, a period of negative half cycle, a period of ¼ cycle from the zero cross point to the peak point, a period of ¼ cycle from the peak point to the zero cross point, and a period of n cycle (n is an integer of one or more) for the specific period.

As there is provided the A/D converter, which converts the instantaneous value of the detection signal of the AC current flowing through the container and the contained liquid and also as there is determined the totaling period of the specific period having the predetermined relation to the waveform of the AC current so that the total value of the digital values corresponding to the absolute values of the instantaneous values of the AC current detected during the totaling period is obtained as aforementioned, variations in the instantaneous value of the AC current due to the existence of the defect in the container are totaled during the totaling period. Thus, even though there is just a small difference between the crest value of the waveform of the AC current obtained when the container has the defect and the crest value of the AC current obtained when the container has no defect, the total value can have a larger difference between them.

Thus, according to the aforementioned method, even though there is generated no large difference between the crest value of the AC current flowing through electrodes when the container has the defect causing the leakage of the liquid of the non-electrolyte sealed therein and that when it has no defect, with the container containing the non-electrolyte, the existence of the defect causing the leakage can be inspected with the high accuracy.

Furthermore, as the total value obtained by successively adding the digital values corresponding to the absolute values of the instantaneous values of the detected AC current during the fixed period as aforementioned is used as the judgment value, a noise which would momentarily overlaps the AC current provides little influence on the judgment value whereby the S/N ratio of the judgment value (the signal to be used for the judgment) is made higher. Thus, the misdetection is prevented and the existence of the defect can be judged with the high precision.

Furthermore, according to the aforementioned method, even though there is an insignificant difference between the crest value of the AC voltage waveform obtained when the container has the defect and the crest value of the AC voltage waveform obtained when the container has no defect, the total value of the digital values corresponding to the absolute values of the instantaneous values of the AC current has the larger difference generated between them so that the existence of the defect can be positively judged. Thus, in the case where the liquid in the container is the electrolyte, the existence of the defect can be positively judged even though the crest value of the AC inspection voltage is set up at the low value to the degree in which the discharge phenomenon arising at the defect portion is kept in the fore-discharge phenomenon. Therefore, the existence of the leakage can be inspected without possible deterioration of the container by making the crest value of the AC inspection voltage lower than that of the prior art.

In the preferred embodiment, there is performed two or more times a total value arithmetical operation process in which there is arithmetically operated the total value of the digital values corresponding to the absolute values of the instantaneous values of the AC current detected from the A/D converter during the specific totaling period having the predetermined relation to the waveform of the AC current. The maximum value of the total values obtained in the respective total value arithmetical operation processes performed two or more times is determined as the judgment value (the value to be judged) and it is judged that the defect exists in the container when the thus determined judgment value exceeds the setting value in the comparison therewith.

As the maximum value of the total values obtained in the respective total value arithmetical operation processes performed two or more times is determined as the judgment value in this manner, the probability of obtaining the information including the existence of the defect can be more improved than that in the case where the total value arithmetical operation process is performed only one time and therefore, the precision of the inspection can be improved.

In the case where the electrodes contact for a short time the containers conveyed by a conveyor in the step of manufacturing the products without stopping conveying the containers, as the maximum value of the total values obtained in the respective total value arithmetical operation processes performed two or more times is used as the judgment value as aforementioned, the probability of obtaining the information including the existence of the defect can be heightened and the precision of the inspection can be improved.

In another preferred embodiment of the invention, there is performed two or more times a total value arithmetical operation process in which there is arithmetically operated the total value of the digital values corresponding to the absolute values of the instantaneous values of the AC current detected from the A/D converter during the specific totaling period having the predetermined relation to the waveform of the AC current, the average value of the total values obtained in the respective total value arithmetical operation processes performed two or more times is determined as the judgment value (the value to be judged) and it is judged that the defect exists in the container when the thus determined judgment value exceeds the setting value in the comparison therewith.

Also in the case where the average value of the total values obtained in the respective total value arithmetical operation processes performed two or more times is determined as the judgment value as aforementioned, the probability of obtaining the information including the existence of the defect can be more improved than that in the case where the total value arithmetical operation process is performed only one time and therefore, the precision of the inspection can be improved.

Moreover, as the average value of the total values obtained two or more times is determined as the judgment value in this manner, the ratio of S/N of the judgment value can be more improved than that in the case where the total value arithmetical operation process is performed only one time.

The leakage inspection apparatus of the present invention is for an insulating container that seals a liquid and relates to the apparatus for inspecting whether the defect causing the leakage of the container exists.

In the invention, there are provided an inspection power source unit to apply an inspection voltage of high AC voltage across the container, a current detector to detect an AC current flowing from the inspection power source unit through the container and the liquid in the container, an A/D converter to digitally convert an instantaneous value of the detected AC current, judgment value arithmetical operation means to arithmetically operate as the judgment value the total value of the digital values corresponding to the absolute values of the instantaneous values of the AC current detected during a totaling period having a fixed relation to the waveform of the AC current and judgment means to compare the judgment value with a setting value to judge that the container has a defect when the judgment value exceeds the setting value.

The aforementioned judgment value arithmetical operation means may be so constructed that there is performed two or more times a total value arithmetical operation processes in which there is arithmetically operated the total value of the digital values corresponding to the absolute values of the instantaneous values of the AC current detected from the A/D converter during the specific totaling period having a fixed relation to the waveform of the detected AC current and the maximum value of the total values obtained in the respective total value arithmetical operation processes performed two or more times is determined as the judgment value.

Also, the aforementioned judgment value arithmetical operation means may be so constructed that there is performed two or more times a total value arithmetical operation processes in which there is arithmetically operated the total value of the digital values corresponding to the absolute values of the instantaneous values of the AC current detected from the A/D converter during the specific totaling period having a fixed relation to the waveform of the detected AC current and the average value of the total values obtained in the respective total value arithmetical operation processes performed two or more times is determined as the judgment value.

It is preferable that a period such as a period of ½ cycle of the waveform of the AC current and a period of n cycle (n is an integer of one or more) is selected as the aforementioned totaling period.

BRIEF DESCRIPTION OF THE DRAWINGS

The above and other objects and features of the invention will be apparent from the detailed description of the preferred embodiments of the invention, which are described and illustrated with reference to the accompanying drawings, in which;

FIG. 6A illustrates an equivalent circuit of the circuit of FIG. 5 when the container has no defect while

DETAILED DESCRIPTION OF PREFERRED EMBODIMENTS

Figure 1:
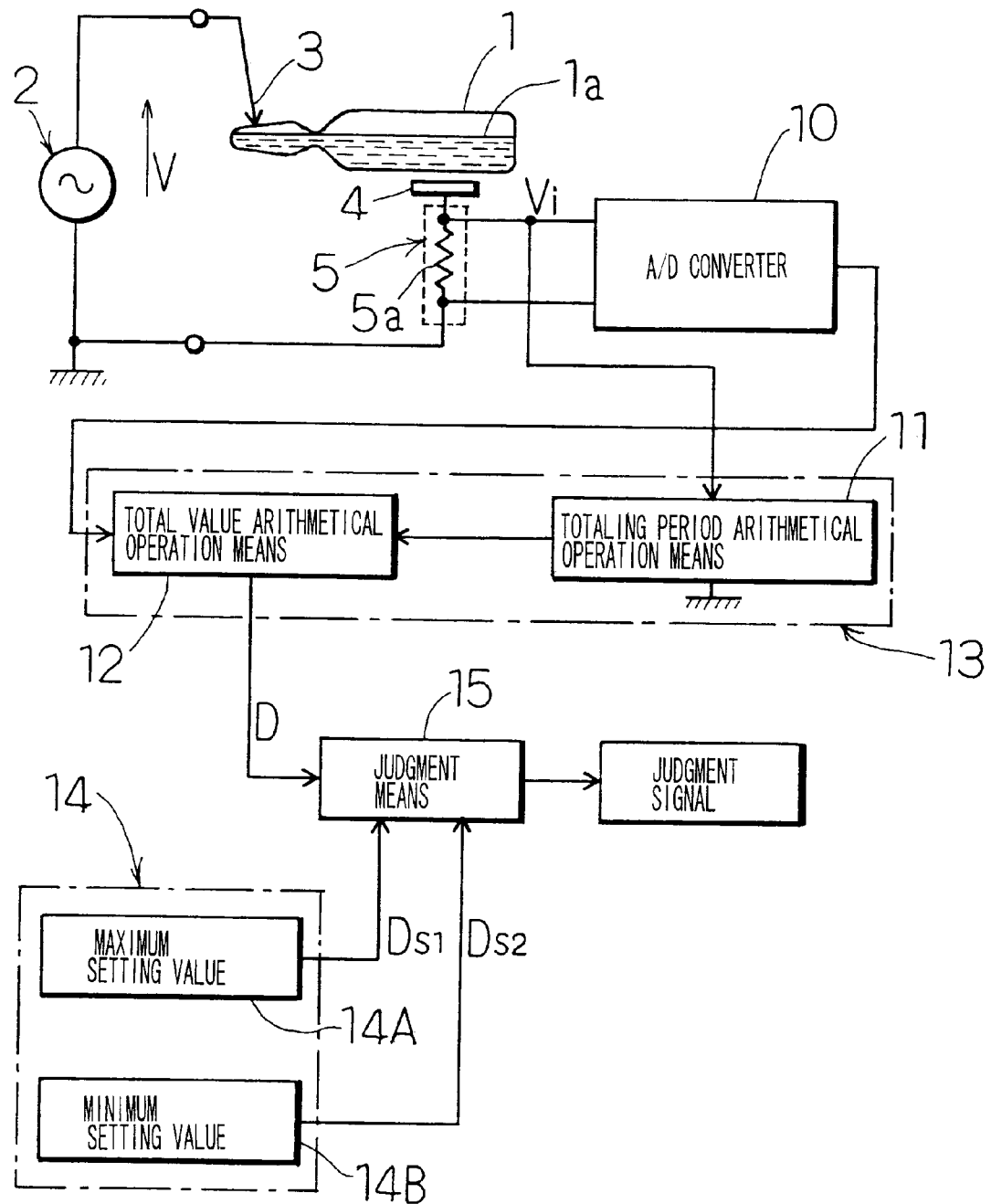
FIG. 1 is a schematic diagram of a leakage inspection apparatus constructed in accordance with an embodiment of the invention.

Referring now to FIG. 1, there is illustrated an embodiment of a leakage inspection apparatus for carrying out a leakage inspection method of the invention. An inspection power source unit is designated by a reference numeral 2 in FIG. 1 and applies a high AC voltage having a fully high crest value as an inspection voltage Vt across a container 1, which is an object of the inspection. A non-ground side electrode 3 and a ground side electrode 4 are engaged with the inspection portions of the container, respectively. A current detecting resistance 5a is inserted between the non-ground side electrode 4 and a ground side output terminal of the inspection power source unit 2.

The configurations of the electrodes and how the electrodes are engaged with the container may be employed in view of those employed for the conventional inspection method.

The container 1 is an insulating one formed of a glass, a plastic material, etc., and a liquid 1a is sealed within the container 1. The illustrated container 1 is shown to be an ampoule for an injection.

As the inspection voltage of high AC voltage is applied across the container from the inspection power source unit 2 as shown in FIG. 1, an AC current flows from the power source unit 2 through the electrodes 3 and 4, through the container 1 and the liquid 1a therein and through the current detection resistance 5a and a current detection signal (a voltage signal) proportional to the AC current is obtained across the current detection resistance 5a.

In the illustrated embodiment, by the current detection resistance 5a, a current detector 5 is formed, which detects the AC current flowing through the container 1 and the contained liquid when the inspection voltage Vt is applied across the container 1.

The frequency and the crest value of the aforementioned inspection voltage may be set at a proper value in accordance with the materials of the container, the quality of the liquid in the container, the size of the container, etc. so that the current of magnitude enough to use for the inspection can flow through the capacity component of the impedance between the electrodes.

The crest value of the inspection voltage is set at a fully high value falling within the range in which there possibly never arises the insulation destruction of the container, which is the object of the inspection. Usually, the voltage approximately between 8 kV and 30 kV may be used for the inspection voltage. The frequency of the inspection voltage may be of a proper one falling within the range from the commercial frequency to hundreds Hz.

Figure 4A:
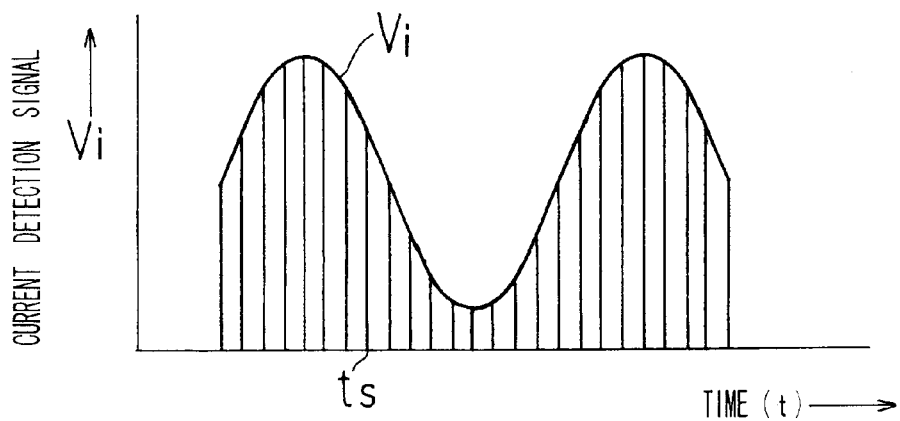
FIGS. 4A through 4C illustrate the operation of the A/D converter.
Figure 4B:
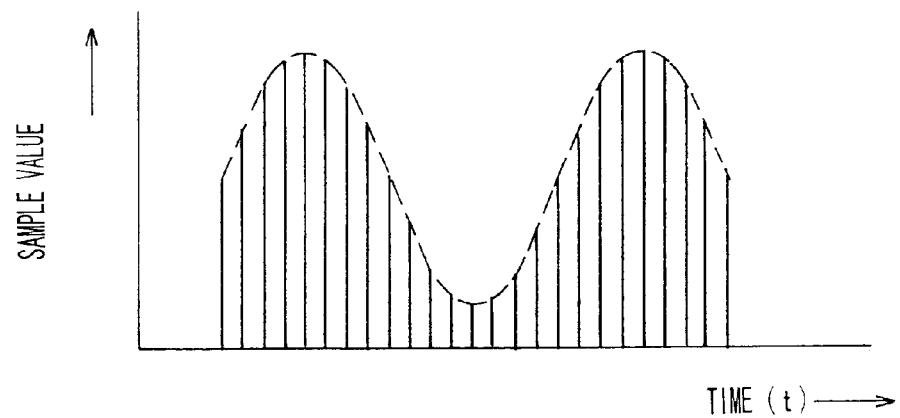

The current detection signal Vi obtained from the current detector 5 is input to an A/D converter 10. The A/D converter 10 samples the current detection signal Vi obtained from the current detector 4 at the predetermined sample timing ts as shown in FIG. 4A, specimenizes the current detection signal and quantizes each of the sample values to convert the instantaneous values of the current detection signal Vi into digital values.

The output of the A/D converter 10 is applied to total value arithmetical operation means 12 together with an output of totaling period detection means 11. The totaling period detection means 11 detects a specific period having a predetermined relation to the waveform of the AC current as a totaling period, based on a zero cross point or a peak point of the waveform of the AC current detected by the current detector 5 and applies an arithmetical operation start command and an arithmetical operation end command to the total value arithmetical operation means 12 at the start and the end of the detected totaling period. The totaling period detection means 11 may comprise a zero cross detection circuit and/or a peak detection circuit and a computer programmed so as to generate the arithmetical operation start command and the arithmetical operation end command in accordance with the detection signal output by these detection circuits, for example.

The totaling period is the one corresponding to the portions used for the judgment among the respective portions of the waveform of the AC current detected by the current detector 5. For instance, in the case where the waveform of positive half cycle of the detected AC current is used for the judgment, the period of the positive half cycle of the AC current is used as the totaling period and in the case where the waveform of one cycle of the detected AC current is used for the judgment, the period of one cycle of the AC current is used as the totaling period.

In the invention, the totaling period may be set so that the same portions as the waveform of the detected AC current is used for the judgment and the portions of the waveform of the AC current to which the totaling period is set so as to correspond can be arbitrarily determined, but the totaling period may be preferably set as a period such as a n/4 cycle period (n is an integer of one or more) or and a n cycle period during which the AC current is detected on a basis of the zero cross or the peak point where the AC current can be more easily detected.

The period of the half cycle of the AC current, the period of the positive half cycle thereof, for example can be detected by detecting the zero cross point arising when the waveform of the AC current shifts from the negative half wave to the positive half wave and the zero cross point arising when the waveform of the AC shift from the positive half wave to the negative half wave.

The period of the one cycle of the AC current can be detected by detecting the zero cross point arising when the waveform of the AC current shifts from the negative half wave to the positive half wave or the zero cross point arising when the waveform of the AC shift from the positive half wave to the negative half wave. The zero cross point and the peak point of the waveform of the AC current can be detected by the conventional means.

The total value arithmetical operation means 12 arithmetically operates the total value of the digital values corresponding to the absolute values of the instantaneous values of the AC current detected during the totaling period in order to obtain the judgment value (the value to be judged). In the case where the totaling period is set as the period of the positive half cycle of the AC current, the total value of the digital values corresponding to the absolute values of the instantaneous values of the AC current can be arithmetically operated by inputting the current detection signal Vi of the AC waveform to the A/D converter 10 to successively adding or totaling the digital values output by the A/D converter during the totaling period thereto as shown in FIG. 4A.

The total value arithmetical operation means 12 may comprise an adder or a computer to start the arithmetical operation when the totaling period detection means 11 generates the arithmetical operation start command to successively add or total the digital values given from the A/D converter 10 and terminates the arithmetical operation when the totaling period detection means 11 generates the arithmetical operation end command.

Figure 4C:
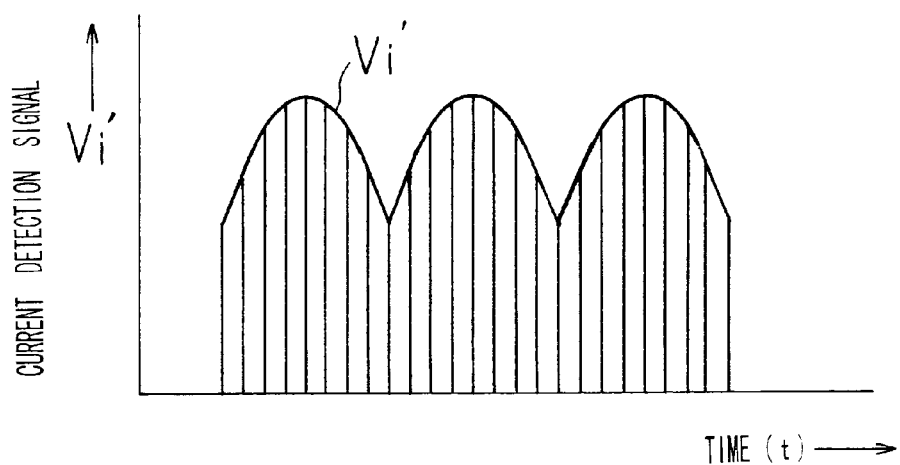

On the other hand, in the case where the totaling period is set as the period of the negative half cycle of the AC current, the total value of the digital values corresponding to the absolute values of the instantaneous values of the AC current can be arithmetically operated by inputting to the A/D converter 10 the current detection signal Vi' obtained by rectifying the full wave of the signal of AC waveform obtained from the both ends of the current detection resistance 5a to successively totaling the digital values output by the A/D converter 10 during the totaling period as shown in FIG. 4C. Also, in this case, the total value arithmetical operation means 12 may comprise an adder so constructed as to start the arithmetical operation in which the input digital values are totaled when the arithmetical operation start command is given and terminate the arithmetical operation when the arithmetical operation end command is given or a computer programmed so that the arithmetical operation to successively total the digital values given from the A/D converter 10 is performed when the arithmetical operation start command is given and the arithmetical operation ends when the arithmetical operation end command is given.

Similarly, in the case where the totaling period is set as the period of n cycles of the AC current, the total value of the digital values corresponding to the absolute values of the instantaneous values of the AC current can be arithmetically operated by inputting to the A/D converter 10 the current detection signal Vi' obtained by rectifying the full wave of the signal of AC waveform obtained from the both ends of the current detection resistance 5a to successively totaling the digital values output by the A/D converter 10 during the totaling period as shown in FIG. 4C.

In the case where the totaling period is set as the period of the negative half cycle of the AC current, the current detection signal input to the A/D converter may be of AC waveform as shown in FIG. 4A and the arithmetical operation may be performed in which the digital values output by the A/D converter are converted into the values corresponding to the absolute values of the instantaneous values of the negative half cycle of the AC current and thereafter the converted digital values may be successively added or totaled. In this case, the total value arithmetical operation means 12 may be provided with signal process means to convert the digital values output by the A/D converter during the period of the negative half cycle of the AC current into the values corresponding to the absolute values of the instantaneous values of the negative half cycle of the AC current. The signal process means can be accomplished by practicing the predetermined program of the computer.

In the embodiment illustrated in FIG. 1, the totaling period detection means 11 and the total value arithmetical operation means 12 constitute judgment value arithmetical operation means 13 to arithmetically operate the total value of the digital values corresponding to the absolute values of the instantaneous values of the AC current detected by the A/D converter 10 during the specific totaling period having the specific relation to the waveform of the AC current and to determine the total value as the judgment value (the value to be judged) D.

In the case where the totaling period is set as the period of the half cycle of the waveform of the AC current, the waveform of the current detection signal input to the A/D converter 10 may be of rectified half waveform of the rectified output appearing only during the half cycle period corresponding to the totaling period instead of AC waveform as shown in FIG. 4A or of full-wave rectified waveform as shown in FIG. 4C.

As the waveform of the current detection signal input to the A/D converter 10 is of the half wave rectified waveform wherein the rectified output appears only during the half cycle period corresponding to the totaling period as aforementioned, the digital value is output from the A/D converter 10 only during the totaling period. Thus, the totaling period detection means 11 may be omitted.

The judgment value (the value to be judged) obtained by being arithmetically operated by the judgment value arithmetical operation means 13 is supplied to judgment means 15 together with a setting value given from setting value generation means 14. In the illustrated embodiment, the setting value generation means 14 comprises maximum setting value generation means 14A to generate the maximum setting value Ds1 and minimum setting value generation means 14B to generate the minimum setting value Ds2. These setting values Ds1 and Ds2 are compared with the judgment value D.

The maximum setting value Ds1 is the one used for judging whether the defect exists in the container or not, while the minimum setting value is the one used for judging whether the container as the objective of the judgment is empty or not or whether the content of the liquid within the container is less than the predetermined amount or not.

As described later, as the defect such as the pinhole or the crack exists in the container, the judgment value D exceeds the maximum setting value Ds1 and as the container is empty or as the content of the liquid within the container is less than the minimum value of the allowable range, the judgment value D gets less than the minimum setting value Ds2. The judgment means 15 outputs the judgment signal indicating that the container is the inferior article when the judgment value D exceeds the setting value Ds1 or when the judgment value is less than the setting value Ds2 and outputs the judgment signal indicating that the container is the good article when the judgment value D is between the setting values Ds1 and Ds2. The judgment signal indicating that the container is the inferior article and the judgment signal indicating that the container is the good article have a level different from each other.

Since the total value arithmetical operation means 12 outputs the judgment value D as the digital value, the judgment means 15 and the setting value generation means 14 may preferably comprise a computer, but they may comprise an analogue circuit and the judgment value converted into an analogue signal may be input to the judgment means 15.

Figure 5:
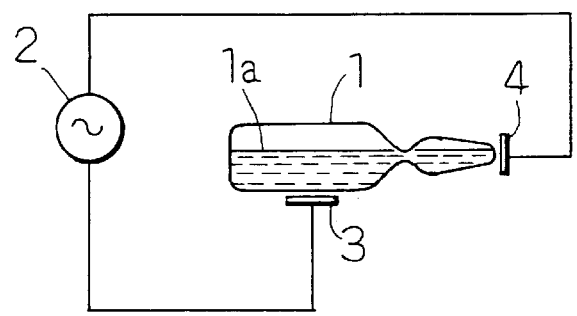
FIG. 5 illustrates a circuit for applying an inspection voltage across a container, which is the object of the inspection.
Figure 6A:
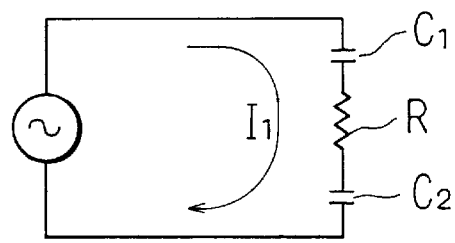

In the case where the circuit is so constructed that the AC high voltage is applied from the inspection power source unit 2 through the electrodes 3 and 4 across both of the insulating container 1 as the inspection objective in which the liquid is sealed and the liquid within the container as shown in FIG. 5, the equivalent circuit is as indicated in FIG. 6A if the liquid is the electrolyte and when the container 1 has no defect. In FIG. 6A, C1 and C2 designate electrostatic capacitances between the electrode 3 and the liquid 1a and between the electrode 4 and the liquid 1a, respectively and R designates a resistance of the liquid.

In the state where such an equivalent circuit is established, an AC current I1 having a frequency equal to the output frequency of the power source unit 2 flows through an impedance of the electrostatic capacitances C1 and C2 and the resistance R. If the frequency of the AC inspection voltage is expressed by "f", the current I1 is given by the following expression.

$$I1 = V/(R + X1 + X2) \quad (1)$$

wherein X1 and X2 are given by the following formulas;

$$X1 = 1/2\pi f C1 \quad (2)$$

$$X2 = 1/2\pi f C2 \quad (3)$$

Figure 6B:
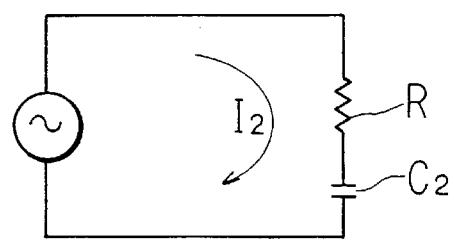
FIG. 6B illustrates an equivalent circuit of the circuit of FIG. 5 when the container has the defect.

On the other hand, if the defect exists in the portion of the container the electrode 3 is engaged with, the electric discharge arises in the defective portion and therefore this is equivalent to the state where the electrostatic capacitance C1 of FIG. 6 gets shorted. Thus, the equivalent circuit is as indicated in FIG. 6B. At this time, an AC current I2 having a frequency equal to the output frequency of the power source unit 2 flows through an impedance of the static capacitance C2 and the resistance R. The AC current I2 is given by the following expression.

$$I2 = V/(R + X2) \quad (4)$$

As apparent from the expressions (1) and (4), the current I2 flowing when there exists the defect in the inspection portion the electrode is engaged with has the value larger than the value of the current I1 flowing when there is no defect therein.

Thus, whether there exists the defect at the portion of the container which the electrodes are engaged with or not can be judged by detecting the AC current I flowing through the container 1 and the liquid therein and judging the magnitude thereof. In this manner, the quality of the container can be judged by repeating the inspection while the electrodes are engaged with the main portions where the defect of the container tends to be produced.

Since the electrostatic capacity C1 of FIG. 6A gets small when there is a small quantity of the liquid in the container 1, the current flowing through the container 1 and the liquid 1a therein gets smaller compared with that when the container 1 contains the liquid of predetermined quantity. Thus, if the judgment value is detected to be smaller than the minimum setting value as a result of comparing the judgment value with the minimum setting value, it can be detected that there is a small quantity of the liquid in the container 1 or that the container 1 is empty.

As aforementioned, since the resistance R of the liquid in the container 1 is small if the liquid is the electrolyte, the electrostatic capacitance C1 nearly gets a state of short-circuit by producing an arc discharge at the portion of the container 1 where the electrodes are engaged with and there is the defect thereat and the equivalent circuit varies as indicated in FIG. 6B. Thus, since there occurs a large difference between the AC current I1 flowing through the container and the liquid therein when there exists no defect in the container and the AC current I2 flowing when there exists the defect, the existence of the defect can be detected by properly setting the threshold value which should be compared with the detection value (the crest value) of the AC current flowing when the inspection voltage is applied.

However, since the resistance R of the liquid of in the container 1 is large if the liquid is the non-electrolyte, there arises no arc discharge and the discharge phenomenon arising in the defective portion is kept at the fore-discharge phenomenon. Thus, it is not possible to arise a clearly distinguishable difference between the AC current flowing when the defect exists and the AC current flowing when no defect exists. Therefore, it is hard to properly set the threshold value for judging the existence of the defect relative to the detected AC current. In this manner, the existence of the defect cannot be positively judged by just comparing the AC current with the threshold value.

On the other hand, according to the invention, as there is obtained the total value of the digital values corresponding to the absolute values of the instantaneous values of the AC current flowing when the inspection voltage is applied across the container 1 by successively adding the digital values over the totaling period having the predetermined relation to the waveform of the AC current, the variations in the instantaneous values of the AC current caused by the existence of the defect are also totaled during the totaling period. Thus, even though the crest value of the AC current obtained when the container has the defect cannot be clearly distinguished from the crest value of the AC current obtained when the container has no defect, a large difference between the total values can be occurred. Therefore, it will be noted that even if the liquid in the container is the non-electrolyte, the method of the invention can positively detect the existence of the defect in the container.

As the total value obtained by successively adding or totaling the digital values corresponding to the absolute values of the instantaneous values of the AC current flowing through the container 1 and the liquid therein over the predetermined period is used as the judgment value D for the judgment, even when a noise is instantaneously mixed with the AC current, it can reduce the influence on the judgment value D whereby the S/N ratio of the judgment value D can be higher. Thus, the precision in the judgment of the existence of the defect can be improved.

In addition thereto, in accordance with the aforementioned method, since there can produced the clearly distinguishable difference between the judgment values D even though there cannot be clearly distinguished the difference between the crest value of the waveform of the AC current when the container 1 has the defect and that when the container has no defect, the existence of the defect can be positively judged even though the crest value of the AC inspection voltage is set at a value lowered to the degree where the discharge phenomenon is kept at the foredischarge phenomenon in the case where the liquid in the container is the electrolyte. Therefore, it will be noted that the existence of the leakage can be inspected without any deterioration of the container by lowering the crest value of the AC inspection voltage in comparison with the prior art.

Although, in the embodiment illustrated in FIG. 1, the total value of the digital values obtained during the totaling period is used as the judgment value as it is, there is two or more times performed the total value arithmetical operation process where there is arithmetically operated the total value of the digital values corresponding to the absolute values of the instantaneous values of the AC current detected from the output of the A/D converter 10 during the totaling period which is the period having the specific relation to the waveform of the detected AC current and the maximum value of the total values obtained by the respective total value arithmetical operation processes performed two or more times may be used as the judgment value.

Figure 2:
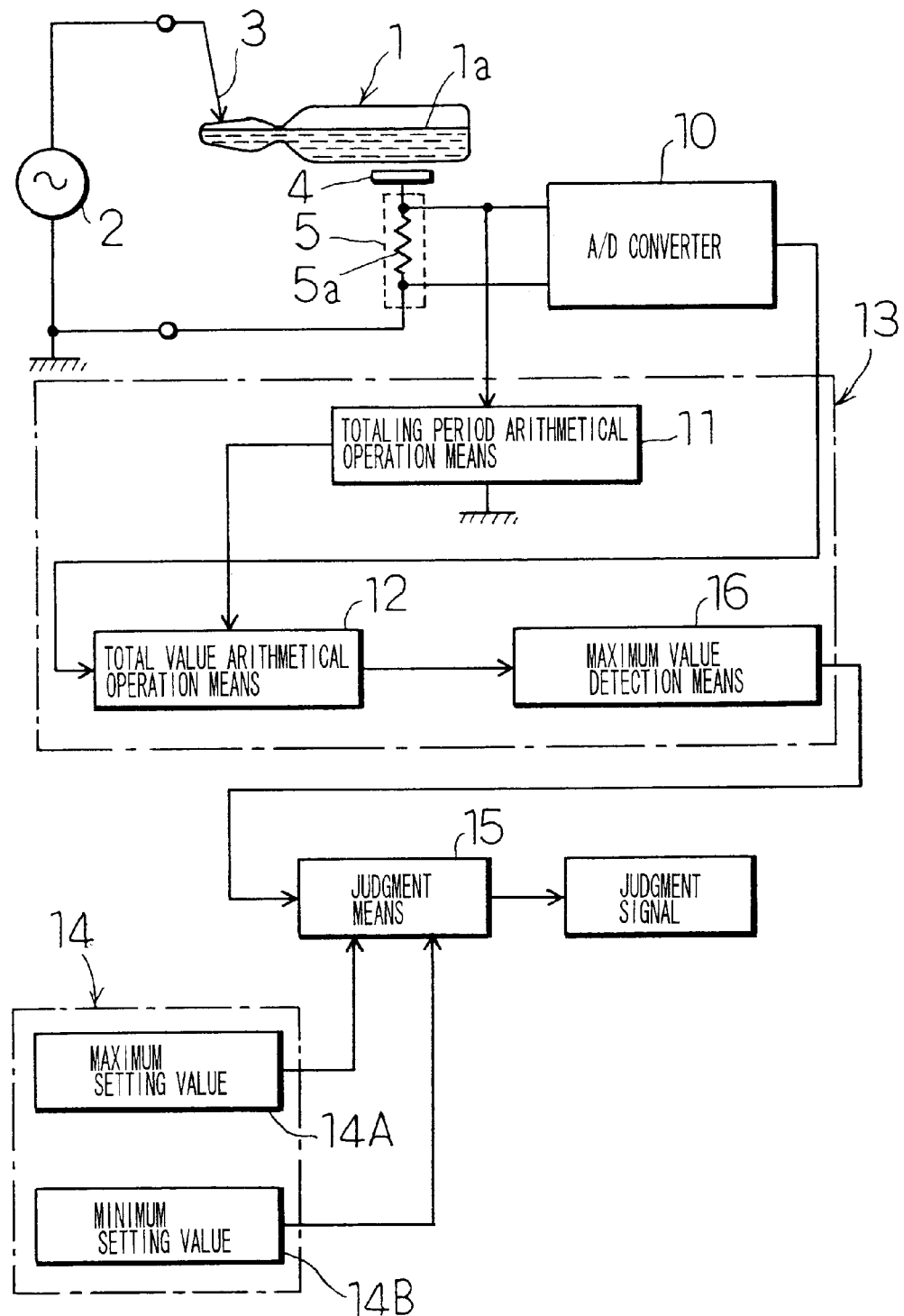
FIG. 2 is a schematic diagram of a leakage inspection apparatus constructed in accordance with another embodiment of the invention.

FIG. 2 illustrates a construction of an inspection apparatus in which the maximum value of the total values obtained in the respective total value arithmetical operation processes performed two or more times is determined as the judgment value. In the embodiment of FIG. 2, the totaling period detection means 11 is so constructed as to generate the arithmetical operation start command and the arithmetical operation end command two or more times and the total value arithmetical operation means 12 is adapted to perform the arithmetical operation process two or more times. There is provided maximum value detection means 16 to obtain the maximum value of the total values obtained in the respective total value arithmetical operation processes performed two or more times. The maximum value of the total values obtained by the maximum value detection means 16 is applied as the judgment value to the judgment means 15. The maximum value detection means 16 may be comprised of a microcomputer, for example.

As the maximum value of the total values obtained in the respective total value arithmetical operation processes performed two or more times is used as the judgment value, the information including the existence of the defect can be more positively obtained in comparison with the case where there is the judgment value obtained when the total value arithmetical operation is performed only once and therefore the precision in the inspection can be more improved.

Also, as the maximum value of the total values obtained in the respective total value arithmetical operation processes performed two or more times is used as the judgment value, even though the inspection is performed while the electrodes are engaged with the container just for a short time without stopping the container under conveyance, the information including the existence of the defect can be obtained with high probability and the precision of the inspection can be improved.

Instead of using as the judgment value the maximum value of the total values obtained in the total value arithmetical operation processes performed two or more times, the average value of the total values obtained in the respective total value arithmetical operation processes performed two or more times may be used as the judgment value. In this case, the leakage inspection apparatus is so constructed as shown in FIG. 3, for example.

Figure 3:
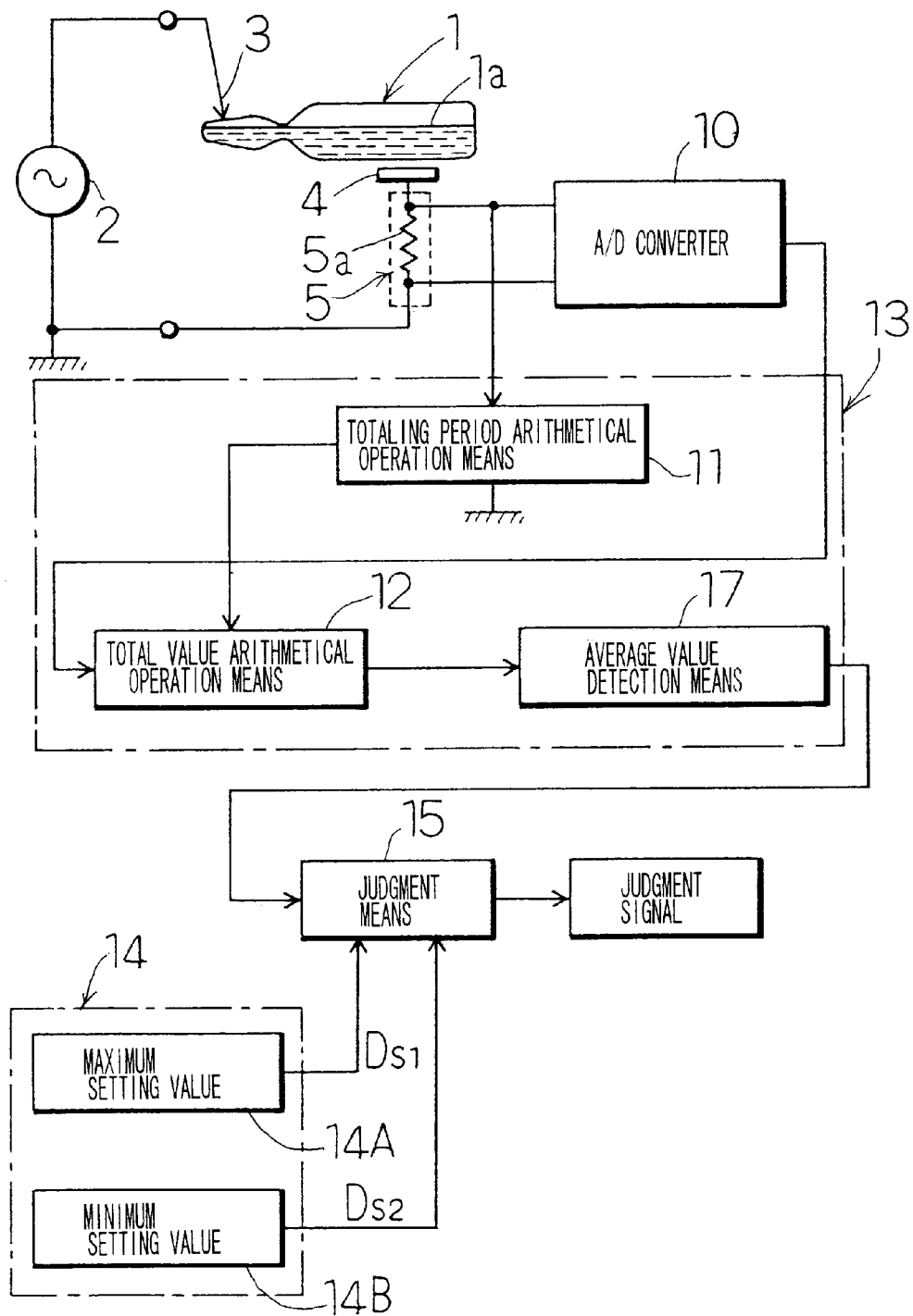
FIG. 3 is a schematic diagram of a leakage inspection apparatus constructed in accordance with further embodiment of the invention.

Also, in the embodiment of FIG. 3, the totaling period detection means 11 is so constructed as to generate the arithmetical operation start command and the arithmetical operation end command two or more times and the total value arithmetical operation means 12 is adapted to perform the arithmetical operation two or more times. There is provided average value detection means 17 to obtain the average value of the total values obtained in the respective total value arithmetical operation processes performed two or more times. The average value of the total values obtained by the average value detection means 17 is applied as the judgment value to the judgment means 15.

Also, as the average value of the total values obtained in the respective total value arithmetical operation processes performed two or more times is used as the judgment value, the information including the existence of the defect can be more positively obtained in comparison with the case where the total value arithmetical operation is performed only once and therefore the precision in the inspection can be more improved.

In addition thereto, as the average value of the total values obtained two or more times is used as the judgment value, the S/N ratio of the judgment value can be more improved in comparison with the case where the total value arithmetical operation is performed only once and therefore the precision in the inspection can be more improved.

The results of the inspection experiments on the container having the non-electrolyte contained as the liquid, which is performed by the inventor, are shown in FIGS. 7 and 8. In these inspection experiments, there was prepared a glass ampoule having a distilled water of 20 [ml] sealed therein as the experiment sample. Also, in the experiments, the crest value of the inspection voltage applied across the ampoule was 23 kV and the frequency thereof was 500 [Hz].

Figure 7A:
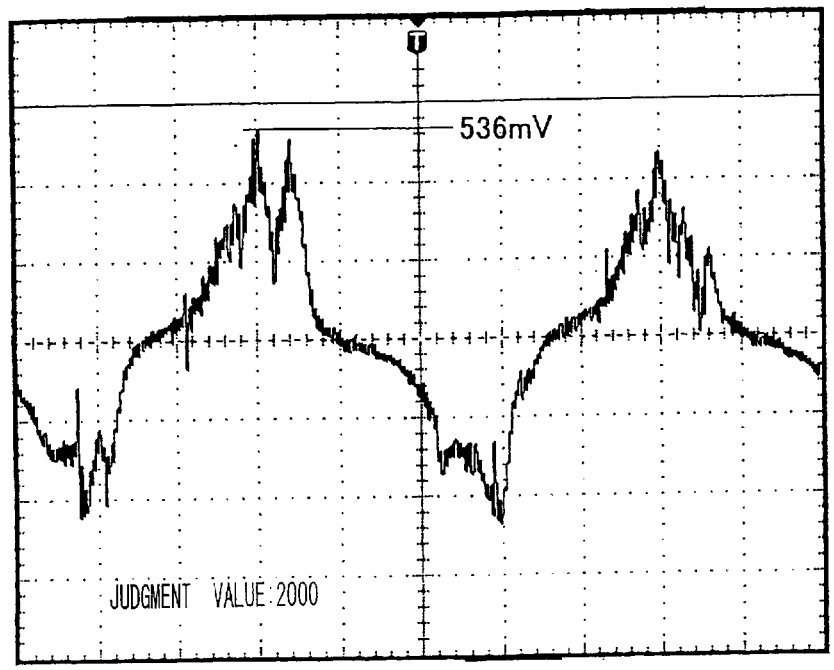
FIGS. 7A and 7B illustrate the actually measured waveforms of the AC current flowing when the inspection voltage is applied across two samples of the good product having no defect, respectively.
Figure 7B:
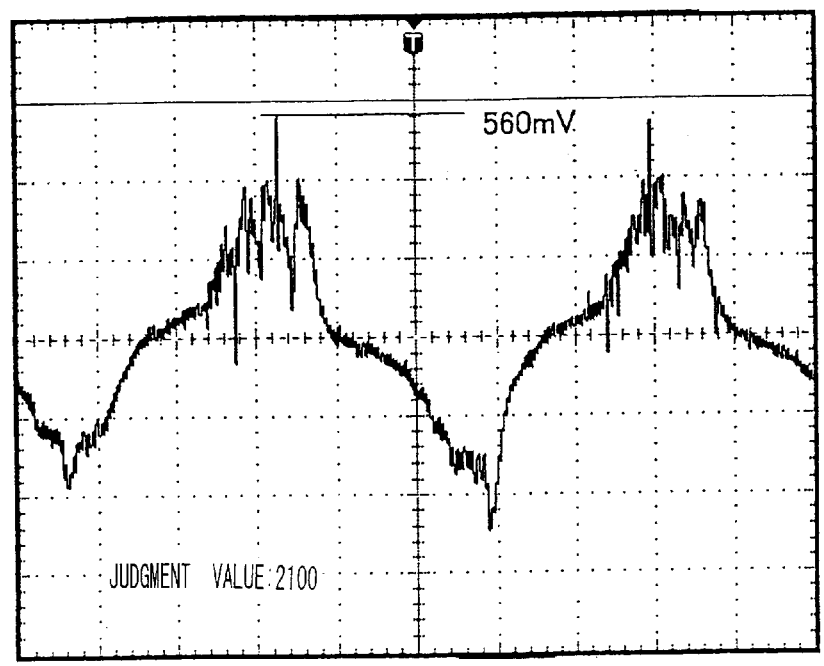

FIGS. 7A and 7B show the waveforms of the current detection signals Vi measured when the inspection voltage was applied across the samples of the two good articles having no defect such as a pinhole or a crack, respectively.

With respect to one of the samples of the good articles showing the waveform of FIG. 7A, the maximum value of the crest value of the waveform of the positive half cycle of the current detection signal Vi was 536 [mV] as indicated in this figure and with respect to the other sample of the good articles showing the waveform of FIG. 7B, the maximum value of the crest value of the waveform of the positive half cycle of the current detection signal Vi was 560 [mV] as indicated in this figure.

Figure 8A:
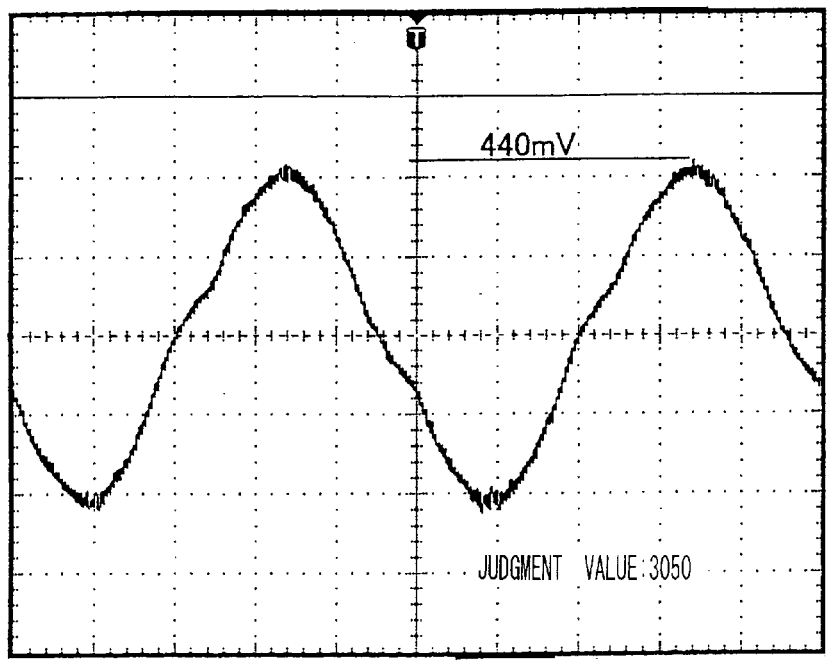
FIGS. 8A and 8B illustrate the actually measured waveforms of the AC current flowing when the inspection voltage is applied across two samples of the inferior product having the defect, respectively.
Figure 8B:
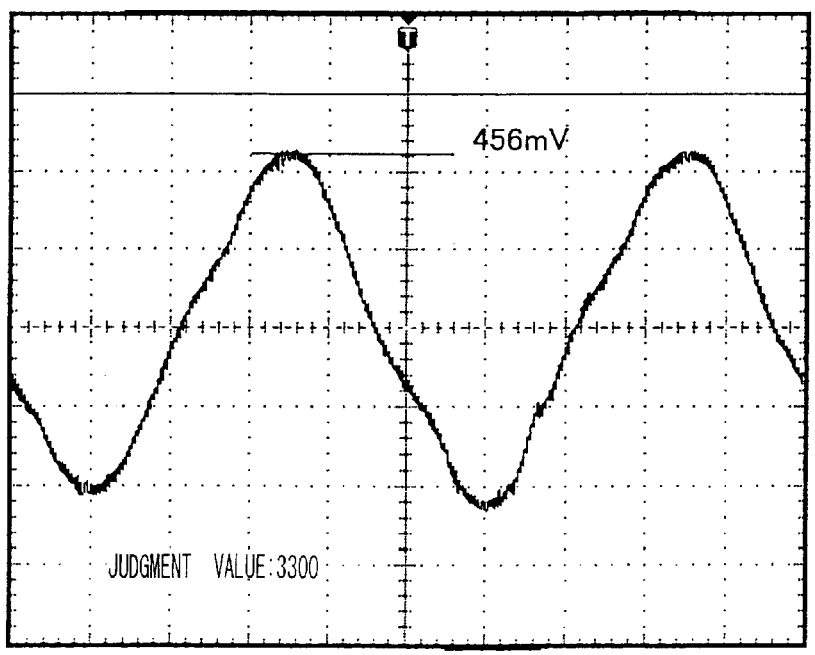

FIGS. 8A and 8B show the waveforms of the current detection signals Vi measured by the detection of the pinholes when the inspection voltage was applied across the samples of the inferior articles having the pinhole formed therein, respectively.

With respect to one of the samples of the inferior articles showing the waveform of FIG. 8A, the maximum value of the crest value of the waveform of the positive half cycle of the current detection signal Vi was 440 [mV] as indicated in this figure and with respect to the other sample of the inferior articles showing the waveform of FIG. 8B, the maximum value of the crest value of the waveform of the positive half cycle of the current detection signal Vi was 456 [mV] as indicated in this figure.

As shown in FIGS. 7 and 8, when the container contains the non-electrolyte such as the distilled water as the liquid, the crest value of the current detection signal obtained by the existence of the defect of the container sometimes gets lower than the crest value of the current detection signal obtained by the non-existence of the defect. Thus, it will be noted that when the container seals the liquid of the non-electrolyte, the existence of the defect cannot be detected by the prior art method of comparing the crest value of the current detection signal with the threshold value.

On the other hand, in the examples of FIGS. 7 and 8, when there was obtained the total value of the digital values corresponding to the absolute values of the instantaneous values of the AC current flowing through the samples from the inspection power source unit during the totaling period of the positive half cycle of the AC current, there appeared a large difference between the total value when the samples were the good articles and the total value when the samples were the inferior articles.

More particularly, with respect to the sample of the good articles as shown in FIG. 7A, when the total value arithmetical operation was performed during the totaling period of the half cycle of the current detection signal having the crest value of 536 [mV] shown, the obtained total value (the judgment value) was 2000. With respect to the sample of the good articles as shown in FIG. 7B, when the total value arithmetical operation was performed during the totaling period of the half cycle of the current detection signal having the crest value of 560 [mV] shown, the obtained total value (the judgment value) was 2100.

On the other hand, with respect to the sample of the inferior articles as shown in FIG. 8A, when the total value arithmetical operation was performed during the totaling period of the half cycle of the current detection signal having the crest value of 440 [mV] shown, the obtained total value (the judgment value) was 3050. With respect to the sample of the inferior articles as shown in FIG. 8B, when the total value arithmetical operation was performed during the totaling period of the half cycle of the current detection signal having the crest value of 456 [mV] shown, the obtained total value (the judgment value) was 3300.

It was confirmed by these results that any of the samples of the inferior articles has the total value substantially larger than any of the ones of the good articles.

In this manner, as there is obtained the total value of the digital values corresponding to the absolute values of the instantaneous values of the current detection signal over the totaling period, which is the specific one having the predetermined relation to the waveform of the AC current detected when the inspection voltage is applied, even though the liquid in the container is the non-electrolyte, the judgment value when the container has the defect is always larger than that when it has no defect and there can be produced the larger difference between the Judgment value obtained when the container has the defect and the judgment value obtained when it has no defect. Thus, the existence of the defect can be positively detected by comparing the judgment values with the proper setting value. The setting value that should be compared with the judgment values may be experimentally determined.

Although, in the embodiments shown in FIGS. 1 through 3, whether the quantity of the liquid in the container is less than the minimum value of the allowance range or not is judged by comparing the judgment value with the minimum setting value, when it is required to inspect only the existence of the leakage of the container (the existence of the defect), the comparison of the judgment value with the minimum setting value can be omitted.

In accordance with the invention, since there arises the clearly distinguishable difference between the judgment value obtained when the container has the defect and that obtained when it has no defect by obtaining as the judgment values the total value of the digital values corresponding to the absolute values of the instantaneous values of the AC current detected during the totaling period, which is the specific period having the predetermined relation to the waveform of the AC current flowing through the container and the liquid therein, the existence of the defect can be precisely detected by the method of the invention even though it cannot be detected from the crest value of the AC current detected when the inspection voltage is applied across the container because the liquid in the container is the non-electrolyte.

Also, in the accordance with the invention, since there is used for the judgment the total value obtained by successively totaling the digital values corresponding to the absolute values of the instantaneous values of the detected AC current during the predetermined period, the noise which would be instantaneously mixed with the AC current can have little influence on the judgment value whereby the S/N ratio of the judgment value increases and therefore the precision with which the existence of the defect is judged can be improved.

Furthermore, in accordance with the invention, since the existence of the defect can be accurately judged by producing the substantial difference between the total values of the digital values corresponding to the absolute values of the instantaneous values of the AC current even though it cannot be clearly detected from the crest value of the AC current flowing through the container and the liquid therein, it can be precisely judged even though the crest value of the AC inspection voltage is set at a lower value so that the discharge phenomenon arising at the defective portion of the container in which the electrolyte is contained is kept in the fore-discharge phenomenon. Thus, the existence of the leakage can be inspected without any deterioration of the container, which is caused by the crest value of the AC inspection voltage lower than that of the prior art.

Although some preferred embodiments of the invention have been described and illustrated with reference to the accompanying drawings, it will be understood by those skilled in the art that they are by way of examples, and that various changes and modifications may be made without departing from the spirit and scope of the invention, which is defined only to the appended claims.

What is claimed is:

1. A leakage inspection method having as an object of an inspection an insulating container in which a liquid is sealed and comprising the steps of applying an inspection voltage of AC high voltage across said container; detecting an AC current flowing through said container and said contained liquid and judging from a detection signal of said AC current whether there exists a defect in said container causing a leakage of said liquid or not, said method further comprising the steps of providing an A/D converter for converting an instantaneous value of the detection signal of the AC current into a digital value; arithmetically operating from an output of said A/D converter a total value of digital values corresponding to the absolute values of said instantaneous values of said AC current detected during a specific totaling period having a specific relation to the waveform of said AC current and comparing said total value as a judgment value with a setting value whereby it is judged that said defect exists in said container when said total value exceeds said setting value.

2. A leakage inspection method having as an object of an inspection an insulating container in which a liquid is sealed and comprising the steps of applying an inspection voltage of AC high voltage across said container; detecting an AC current flowing through said container and said contained liquid and judging from a detection signal of said AC current whether there exists a defect in said container causing a leakage of said liquid or not, said method further comprising the steps of providing an A/D converter for converting an instantaneous value of the detection signal of the AC current into a digital value; performing two or more times a total value arithmetical operation process in which there is arithmetically operated from an output of said A/D converter a total value of digital values corresponding to the absolute values of said instantaneous values of said AC current detected during a specific totaling period having a specific relation to the waveform of said AC current; determining as a judgment value a maximum value of said total values obtained by said total value arithmetical operation process performed two or more times and comparing said judgment value with a setting value whereby it is judged that said defect exists in said container when said judgment value exceeds said setting value.

3. A leakage inspection method having as an object of an inspection an insulating container in which a liquid is sealed and comprising the steps of applying an inspection voltage of AC high voltage across said container; detecting an AC current flowing through said container and said contained liquid and judging from a detection signal of said AC current whether there exists a defect in said container causing a leakage of said liquid or not, said method further comprising the steps of providing an A/D converter for converting an instantaneous value of the detection signal of the AC current into a digital value; performing two or more times a total value arithmetical operation process in which there is arithmetically operated from an output of said A/D converter a total value of digital values corresponding to the absolute values of said instantaneous values of said AC current detected during a specific totaling period having a specific relation to the waveform of said AC current; determining as a judgment value an average value of said total values obtained by said total value arithmetical operation process performed two or more times and comparing said judgment value with a setting value whereby it is judged that said defect exists in said container when said judgment value exceeds said setting value.

4. A leakage inspection method for a sealed container as set forth in either of claims 1 through 3 and wherein said totaling period is a period of half cycle of the waveform of said AC current.

5. A leakage inspection method for a sealed container as set forth in either of claims 1 through 3 and wherein said totaling period is a period of n cycle of the waveform of said AC current (n is an integer of one or more).

6. A leakage inspection apparatus having as an object of an inspection an insulating container in which a liquid is sealed and inspecting whether a defect causing the leakage of said container exists or not and comprising an inspection power source unit to apply an inspection voltage of AC high voltage across said container; a current detector to detect an AC current flowing from said inspection power source unit through said container and said liquid in said container; an A/D converter to digitally convert an instantaneous value of current detection signal obtained by said current detector, judgment value arithmetical operation means to arithmetically operate from an output of said A/D converter as a judgment value a total value of the digital values corresponding to the absolute values of the instantaneous values of said AC current detected during a totaling period having a specific relation to the waveform of said AC current and judgment means to compare said judgment value with a setting value to judge that said container has a defect when said judgment value exceeds said setting value.

7. A leakage inspection apparatus having as an object of an inspection an insulating container in which a liquid is sealed and inspecting whether a defect causing the leakage of said container exists or not and comprising an inspection power source unit to apply an inspection voltage of AC high voltage across said container; a current detector to detect an AC current flowing from said inspection power source unit through said container and said liquid in said container; an A/D converter to digitally convert an instantaneous value of current detection signal obtained by said current detection, judgment value arithmetical operation means to perform two or more times a total value arithmetical operation process in which there are arithmetically operated from an output of said A/D converter total values of the digital values corresponding to the absolute values of the instantaneous values of said AC current detected during a totaling period having a specific relation to the waveform of said AC current and determine as a judgment value a maximum value of said total values obtained by said total value arithmetical operation processes performed two or more times and judgment means to compare said judgment value with a setting value to judge that said container has a defect when said judgment value exceeds said setting value.

8. A leakage inspection apparatus having as an object of an inspection an insulating container in which a liquid is sealed and inspecting whether a defect causing the leakage of said container exists or not and comprising an inspection power source unit to apply an inspection voltage of AC high voltage across said container; a current detector to detect an AC current flowing from said inspection power source unit through said container and said liquid in said container; an A/D converter to digitally convert an instantaneous value of current detection signal obtained by said current detector, judgment value arithmetical operation means to perform two or more times a total value arithmetical operation process in which there are arithmetically operated from an output of said A/D converter total values of the digital values corresponding to the absolute values of the instantaneous values of said AC current detected during a totaling period having a specific relation to the waveform of said AC current and determine as a judgment value an average of said total values obtained by said total value arithmetical operation processes performed two or more times and judgment means to compare said judgment value with a setting value to judge that said container has a defect when said judgment value exceeds said setting value.

9. A leakage inspection apparatus for a sealed container as set forth in either of claims 6 through 8 and wherein said totaling period is a period of half cycle of the waveform of said AC current.

10. A leakage inspection apparatus for a sealed container as set forth in either of claims 6 through 8 and wherein said totaling period is a period of n cycle of the waveform of said AC current (n is an integer of one or more).

* * * * *